United States Patent
Awatani et al.

(10) Patent No.: US 11,750,729 B2
(45) Date of Patent: *Sep. 5, 2023

(54) PORTABLE TERMINAL DEVICE, INCOMING CALL SCREEN DISPLAY METHOD, AND PROGRAM

(71) Applicant: NEC Platforms, Ltd., Kawasaki (JP)

(72) Inventors: Tomoki Awatani, Kanagawa (JP); Hikaru Ogawa, Kanagawa (JP)

(73) Assignee: NEC Platforms, Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/883,754

(22) Filed: Aug. 9, 2022

(65) Prior Publication Data
US 2022/0385759 A1  Dec. 1, 2022

Related U.S. Application Data

(63) Continuation of application No. 16/977,678, filed as application No. PCT/JP2020/006621 on Feb. 19, 2020, now Pat. No. 11,457,105.

(30) Foreign Application Priority Data

Mar. 26, 2019 (JP) .................................. 2019-058981
Jan. 15, 2020 (JP) .................................. 2020-004124

(51) Int. Cl.
*H04M 1/57* (2006.01)
*H04M 3/42* (2006.01)
(Continued)

(52) U.S. Cl.
CPC .............. *H04M 1/576* (2013.01); *G06F 3/14* (2013.01); *G16H 10/60* (2018.01); *G16H 40/67* (2018.01);
(Continued)

(58) Field of Classification Search
CPC ........ H04M 1/576; H04M 1/57; H04M 1/724; H04M 3/42042; H04M 19/041;
(Continued)

(56) References Cited

U.S. PATENT DOCUMENTS 5,754,960 A * 5/1998 Downs ................. H04W 84/08
379/267
6,226,512 B1   5/2001 Macaulay et al.
(Continued)

FOREIGN PATENT DOCUMENTS

CN   101984683 A   3/2011
CN   104320532 A   1/2015
(Continued)

OTHER PUBLICATIONS

Australian Office Action for AU Application No. 2020223712 dated Jun. 4, 2021.
(Continued)

*Primary Examiner* — Farid Seyedvosoghi
(74) *Attorney, Agent, or Firm* — Sughrue Mion, PLLC

(57) ABSTRACT

Incoming call signal reception means receives an incoming call signal including a caller number, caller information, and ring type information. Image generation means generates, based on the incoming call signal, a caller information image including at least a portion of the caller information as character information. Telephone dictionary registering means registers the caller number, caller text information, and the caller information image in a telephone dictionary. Incoming call screen display means receives the caller number and acquires the registered caller text information and the caller information image corresponding to the received caller number from the telephone dictionary.
(Continued)

Incoming call screen display means displays an incoming call screen including the caller text information and the caller information image.

12 Claims, 9 Drawing Sheets

(51) Int. Cl.
| | |
|---|---|
| *G16H 40/67* | (2018.01) |
| *G16H 10/60* | (2018.01) |
| *G16H 80/00* | (2018.01) |
| *H04M 1/724* | (2021.01) |
| *G06F 3/14* | (2006.01) |
| *H04M 19/04* | (2006.01) |
| *H04L 65/1053* | (2022.01) |
| *H04M 11/02* | (2006.01) |
| *H04W 84/16* | (2009.01) |

(52) U.S. Cl.
CPC ............ *G16H 80/00* (2018.01); *H04M 1/57* (2013.01); *H04M 1/724* (2021.01); *H04M 3/42042* (2013.01); *H04M 3/42051* (2013.01); *H04M 3/42314* (2013.01); *H04M 19/041* (2013.01); *H04L 65/1053* (2013.01); *H04M 11/027* (2013.01); *H04M 2250/60* (2013.01); *H04W 84/16* (2013.01)

(58) Field of Classification Search
CPC ............ H04M 19/04; H04M 11/027; H04M 2250/60; H04M 1/27453; H04M 1/27475; H04M 1/2753; H04M 1/2757; H04M 1/72484; H04M 1/575; H04M 1/00; H04M 1/2745; H04M 3/42051; H04M 3/42314; G06F 3/14; G16H 10/60; G16H 40/67; G16H 80/00; H04L 65/1053; H04L 65/1073; H04L 65/1046; H04L 65/1069; H04W 84/16; A61G 12/00
See application file for complete search history.

(56) References Cited

U.S. PATENT DOCUMENTS

| | | | |
|---|---|---|---|
| 7,734,028 B2 | 6/2010 | Dhara et al. | |
| 2002/0021790 A1 | 2/2002 | Corbett | H04M 1/57 |
| | | | 379/93.23 |
| 2007/0152811 A1* | 7/2007 | Anderson | G08B 21/0453 |
| | | | 340/539.11 |
| 2009/0170487 A1 | 7/2009 | Ding | |
| 2010/0062714 A1 | 3/2010 | Ozaki | H04M 1/6075 |
| | | | 455/41.3 |
| 2011/0159865 A1 | 6/2011 | Nakao | H04M 1/575 |
| | | | 455/418 |
| 2013/0148646 A1* | 6/2013 | Efrati | H04M 3/42042 |
| | | | 370/352 |
| 2017/0061090 A1* | 3/2017 | Itoh | H04W 4/02 |
| 2017/0135889 A1 | 5/2017 | Omi et al. | |
| 2017/0221344 A1 | 8/2017 | Cox et al. | |
| 2017/0308650 A1 | 10/2017 | Brill et al. | |
| 2018/0070290 A1 | 3/2018 | Breaux | H04M 1/72463 |

FOREIGN PATENT DOCUMENTS

| | | |
|---|---|---|
| CN | 104767858 A | 7/2015 |
| CN | 107734157 A | 2/2018 |
| CN | 207541954 U | 6/2018 |
| CN | 108540655 A | 9/2018 |
| CN | 108933868 A | 12/2018 |
| EP | 1973307 A1 | 9/2006 |
| JP | 2004-201221 A | 7/2004 |
| JP | 2004-343543 A | 12/2004 |
| JP | 2009-147619 A | 7/2009 |
| JP | 2010-232758 A | 10/2010 |
| JP | 2010-263294 A | 11/2010 |
| JP | 2012-199741 A | 10/2012 |
| JP | 2014-103661 A | 6/2014 |
| JP | 2016-220806 A | 12/2016 |
| JP | 2018-86149 A | 6/2018 |
| KR | 10-2018-0110575 A | 10/2018 |

OTHER PUBLICATIONS

Australian Office Action for AU Application No. 2020227110 dated May 3, 2021.
Morey, A. et al, 'Composition of New Features into a Wireless Nurse Call System', Norwegian University of Science and Technology, Department of Telematics, Jan. 2011.
Ascom Wireless Solutions, "How smart devices and Middleware integration are revolutionizing healthcare", Smart devices and Healthcare, white paper, 2016.
Chinese Office Action for CN Application No. 2020800001806.9 dated Mar. 25, 2021 with English Translation.
Supplementary European Search Report for EP Application No. 20760743.3 dated Feb. 2, 2021.
Supplementary European Search Report for EP Application No. 20194045.9 dated Feb. 2, 2021.
Extended European Search Report for EP Application No. 20194052.5 dated Jan. 28, 2021.
International Search Report for PCT/JP2020/006621 dated Mar. 24, 2020 (PCT/ISA/210).
Canadian Examination Report for CA Application No. 3092705, dated Nov. 4, 2022.
Canadian Office Action for CA Application No. 3,092,705, dated May 24, 2023.

\* cited by examiner

| TELEPHONE DICTIONARY | RING TYPE INFORMATION | RINGTONE SETTING |
|---|---|---|
| 1 | 1 | RINGTONE A |
| 2 | 2 | RINGTONE B |
| 3 | 3 | RINGTONE C |

Fig. 8A

| HISTORY NUMBER | INCOMING CALL NUMBER | DISPLAY NAME | INCOMING TIME |
|---|---|---|---|
| 1 | 1000 | TANAKA | 11/29 9:00 |
| 2 | 1000 | TANAKA | 11/29 10:00 |

Fig. 8B

| HISTORY NUMBER | INCOMING CALL NUMBER | DISPLAY NAME | INCOMING TIME |
|---|---|---|---|
| 1 | 1000 | SUZUKI | 11/29 9:00 |
| 2 | 1000 | SUZUKI | 11/29 10:00 |
| 3 | 1000 | SUZUKI | 11/30 15:00 |

Fig. 9

| HISTORY NUMBER | INCOMING CALL NUMBER | DISPLAY NAME | LocalizeCallerName | INCOMING TIME |
|---|---|---|---|---|
| 1 | 1000 | TANAKA | TANAKA | 11/29 9:00 |
| 2 | 1000 | TANAKA | TANAKA | 11/29 10:00 |
| 3 | 1000 | SUZUKI | SUZUKI | 11/30 15:00 |

PORTABLE TERMINAL DEVICE, INCOMING CALL SCREEN DISPLAY METHOD, AND PROGRAM

CROSS-REFERENCE TO RELATED APPLICATIONS

The present application is a continuation application of U.S. patent application Ser. No. 16/977,678 filed on Sep. 2, 2020, which is a National Stage Entry of international application No. PCT/JP2020/006621 filed on Feb. 19, 2020, which claims the benefit of priority from Japanese Patent Application No. 2019-058981 filed on Mar. 26, 2019, and Japanese Patent Application No. 2020-004124 filed on Jan. 15, 2020, the disclosures of all of which are incorporated in their entirety by reference herein.

TECHNICAL FIELD

The present disclosure relates to a portable terminal device, an incoming call screen display method, and a program.

Further, the present disclosure relates to a portable terminal device, an incoming call history display method, and a program.

BACKGROUND ART

A nurse call system which enables telephone conversations between a nurse call extension unit and a portable terminal device carried by a medical worker such as a doctor and a nurse is known. The nurse call system includes a nurse call extension unit (call button), a nurse call base unit, a private branch exchange (PBX), and a Personal Handy-Phone System (PHS) terminal under control of the PBX. A nurse carries a PHS terminal and responds to a nurse call of a patient. When there is a nurse call, the PHS terminal displays a patient name and an extension number. In this case, the nurse can recognize where the call was made from and respond to it.

With the improvement of the radio wave environment of Wi-Fi, the linkage with electronic medical records, and the downsizing of the PHS business, there is an increasing demand for replacing PHS terminals, which are terminals carried by nurses, with smartphones and enabling nurses to respond to a nurse call using the smartphones. Further, there is a need for a medical worker to display an incoming call screen including patient information related to symptoms of a patient on a portable terminal device when an incoming call is received on the portable terminal device side. In this connection, Patent Literature 1 discloses a nurse call system in which a portable terminal device such as a smartphone is used.

In Patent Literature 1, a patient calls a medical worker by pressing a call button provided on a nurse call extension unit. The nurse call extension unit outputs a call signal when a patient presses a call button. The nurse call controller identifies the nurse call extension unit in which the call button is depressed, and refers to the patient information table to acquire the patient name. The nurse call controller transmits the call signal and the patient name to the portable terminal device. The portable terminal device displays an incoming call screen including the extension number of the nurse call extension unit and the patient name on a display screen.

In Patent Literature 1, an incoming call screen is generated by using a telephone directory server. The telephone directory server receives patient information of the patient who presses the call button. The telephone directory server associates the received patient information with an extension number and records it in a telephone directory table. The telephone directory server generates an incoming call screen on the basis of patient information recorded in a telephone directory table and records the incoming call screen. The incoming call screen includes a patient name, an extension number, a medical treatment subject, and a rescue category. The telephone directory server transmits URL (uniform resource locator) information accessible to the recorded incoming call screen to the portable terminal device. The mobile terminal device acquires the incoming call screen from the telephone directory server on the basis of the URL information, and displays the incoming call screen and the call screen in combination on a display screen.

CITATION LIST

Patent Literature

Patent Literature 1: Japanese Unexamined Patent Application Publication No. 2018-86149

SUMMARY OF INVENTION

Technical Problem

In a normal environment, each extension number is often used fixedly by each user. Therefore, in the management of user information (name, e-mail address, etc.) in association with an extension number, there are few use cases in which the user information corresponding to each extension number is frequently changed. However, in the medical field, hospitalization, discharge from hospital, transfer to hospital room, etc. occur according to the situation of the patient. For this reason, the extension number cannot be used in a fixed manner.

In a nurse call system, if the combination of the caller's extension number and patient information is managed for each terminal and the information in the terminal is updated every time the combination is updated, it is necessary to update the information frequently in each terminal. Therefore, when a smartphone terminal is used as a nurse call receiving terminal, it is required, for the nurse call system, that the combination of the caller's extension number and patient information be changed irregularly and the patient information be updated and reflected immediately, as a system requirement. A system that satisfies this requirement can be realized by linking the nurse call terminal with the shared telephone directory linked with the nurse call base unit and the PBX.

Further, the nurse call receiving terminal is desired to have a function of displaying the patient information of the calling patient in response to the received nurse call. For example, when the patient information is displayed on the nurse call receiving terminal, the medical worker can recognize from which patient the nurse call is received and respond to it. In Patent Literature 1, an incoming call screen is generated using a telephone directory server, and the portable terminal device acquires the incoming call screen from the telephone directory server at the time of an incoming call and displays it on a display unit. Thus, the work efficiency of the medical worker can be improved.

By the way, smartphones are divided into two main categories: the iPhone (registered trademark) sold by Apple and the Android (registered trademark) sold by various companies, which is compatible with OS (Operating System), the basic outline of which is regulated by Google. Of these two devices, iPhone devices are particularly in demand in the medical field.

When the iPhone device is used as a nurse call receiving terminal, a VoIP (Voice over Internet Protocol) application for making nurse call telephone conversations can be operated on the iPhone device. However, when the inventors examined the use of an iPhone device as a terminal for receiving a nurse call, the present inventors found that patient information cannot be freely displayed on the receiving screen due to restrictions of the OS.

In the iPhone device, a telephone function application is already installed in the OS, and incoming and outgoing calls of that application are controlled by "CallKit". A VoIP application (also referred to as a dedicated VoIP application) for making nurse call telephone conversations can use CallKit to control incoming and outgoing calls. However, when CallKit is used, the incoming call screen will be the CallKit call screen. CallKit has a restriction that the character information which can be displayed on the incoming call screen is limited. CallKit also has a restriction that the background color on the incoming call screen cannot be changed.

When a dedicated VoIP application does not use CallKit, an incoming call screen can be freely generated and patient information can be displayed on the incoming call screen when a nurse call arrives. However, without CallKit, if an incoming call occurs in the OS's phone function application during telephone conversations of a dedicated VoIP application, the OS's phone function application takes precedence and the telephone conversation are cut off. Further, when an incoming call is received during the security locking of the terminal, the user must first release the security lock, whereby usability is significantly reduced. Thus, the use of CallKit is essential for the operation of a dedicated VoIP application in order to manage conflicting operations with other telephone conversation applications and to respond to incoming calls when the terminal security is locked.

In Patent Literature 1, a dedicated incoming call screen is displayed on a display unit, and thus a function (framework), such as CallKit, for managing conflicting operations with other telephone conversation application and receiving an incoming call during a terminal security lock cannot be used for receiving a nurse call. Therefore, there is a need for a mechanism that enables the display of patient information or the like while utilizing such a framework when receiving a nurse call.

In one aspect, the present disclosure aims to provide a portable terminal device, an incoming call screen display method, and a program capable of displaying information of a caller or the like when receiving a call even in a situation where a combination of a caller number and a caller can be changed.

In another aspect, the present disclosure aims to provide a portable terminal device, an incoming call history display method, and a program capable of correctly displaying information of a caller at the time of receiving a call in an incoming call history while information of a caller or the like can be displayed when receiving a call.

Solution to Problem

In one aspect, the present disclosure provides a portable terminal device including:
incoming call signal reception means for receiving an incoming call signal including a caller number, caller information, and ring type information when an incoming telephone call is received,
image generation means for generating, based on the incoming call signal received by the incoming call signal reception means, a caller information image including at least a portion of the caller information included in the incoming call signal as character information,
telephone dictionary registering means for generating caller text information based on at least one of the caller information and the ring type information, and registering the caller number, the caller text information, and the caller information image in a telephone dictionary managed in the portable terminal device, and
incoming call screen display means for receiving the caller number, acquiring the registered caller text information and the caller information image corresponding to the received caller number from the telephone dictionary, and displaying an incoming call screen including the caller text information and the caller information image.

The present disclosure also provides an incoming call screen display method, including:
receiving an incoming call signal including a caller number, caller information, and ring type information when an incoming telephone call is received, and generating, based on the received incoming call signal, a caller information image including at least a portion of the caller information included in the incoming call signal as character information;
generating caller text information based on at least one of the caller information and the ring type information;
registering the caller number, the caller text information, and the caller information image in a telephone dictionary managed in the portable terminal device;
acquiring the registered caller text information and the caller information image corresponding to the caller number from the telephone dictionary; and
displaying an incoming call screen including the caller text information and the caller information image.

The present disclosure further provides a program causing a processor to execute:
receiving an incoming call signal including a caller number, caller information, and ring type information when an incoming telephone call is received, and generating, based on the received incoming call signal, a caller information image including at least a portion of the caller information included in the incoming call signal as character information,
generating caller text information based on at least one of the caller information and the ring type information,
registering the caller number, the caller text information, and the caller information image in a telephone dictionary managed in the portable terminal device, and
causing a frame work, which is configured to acquire information from the telephone dictionary to generate an incoming call screen and display the incoming call screen, to acquire the registered caller text information and the caller information image corresponding to the caller number from the telephone dictionary, and to display an incoming call screen including the caller text information and the caller information image.

In another aspect, the present disclosure provides a portable terminal device including:

incoming call signal reception means for receiving an incoming call signal including a caller number, caller information, and ring type information when an incoming telephone call is received, telephone dictionary registering means for generating caller text information based on at least one of the caller information and the ring type information, associating the caller number with the caller text information, and registering the caller number and the caller text information in a telephone dictionary managed in the portable terminal device, incoming call screen display means for receiving the caller number, acquiring the registered caller text information corresponding to the received caller number from the telephone dictionary, and displaying an incoming call screen including the caller text information, incoming call history recording means for associating the caller number which is a source of a call with the caller text information and storing the caller number and the caller text information in incoming call history information, and incoming call history display means for displaying an incoming call history including a number of a source of the incoming telephone call and a name of the source of the incoming telephone call, and wherein:

the telephone dictionary registering means deletes, after the incoming telephone call ends, the caller number which the telephone dictionary registering means registered from the telephone dictionary, and the incoming call history display means acquires the caller text information from the incoming call history information and displays the acquired caller text information as a name of the source of a call when displaying the incoming call history.

The present disclosure provides an incoming call history display method including:

receiving an incoming call signal including a caller number, caller information, and ring type information when an incoming telephone call is received, generating caller text information based on at least one of the caller information and the ring type information, registering the caller number and the caller text information in a telephone dictionary managed in the portable terminal device, acquiring the caller text information corresponding to the registered caller number from the telephone dictionary, and displaying an incoming call screen including the caller text information, associating the caller number which is a source of a call with the caller text information and storing the caller number and the caller text information in incoming call history information, and deleting, after the incoming telephone call ends, the registered caller number from the telephone dictionary, and acquiring, when an incoming call history including a number of a source of the incoming telephone call and a name of the source of the incoming is displayed, the caller text information from the incoming call history information and displaying the acquired caller text information as a name of the source of a call.

The present disclosure provides a program causing a processor to execute:

receiving an incoming call signal including a caller number, caller information, and ring type information when an incoming telephone call is received, generating caller text information based on at least one of the caller information and the ring type information, registering the caller number and the caller text information in a telephone dictionary managed in the portable terminal device, acquiring the registered caller text information corresponding to the caller number from the telephone dictionary, and displaying an incoming call screen including the caller text information, associating the caller number which is a source of a call with the caller text information and storing the caller number and the caller text information in incoming call history information, and deleting, after the incoming telephone call ends, the registered caller number from the telephone dictionary, and acquiring, when an incoming call history including a number of a source of the incoming telephone call and a name of the source of the incoming is displayed, the caller text information from the incoming call history information and displaying the acquired caller text information as a name of the source of a call.

Advantageous Effects of Invention

In one aspect, a portable terminal device, an incoming call screen display method, and a program according to the present disclosure can display information of a caller or the like when receiving a call even in a situation where a combination of a caller number and a caller can be changed.

In another aspect, a portable terminal device, an incoming call history display method, and a program according to the present disclosure can correctly display information of a caller at the time of receiving a call in an incoming call history while information of a caller or the like can be displayed when receiving a call.

BRIEF DESCRIPTION OF DRAWINGS

FIG. 8A is a diagram showing an example of the incoming call history display in a certain situation.

FIG. 8B is a diagram showing an example of the incoming call history display in another situation.

FIG. 9 is a diagram showing an example of an incoming call history display in an embodiment of the present disclosure.

DESCRIPTION OF EMBODIMENTS

Figure 1A:
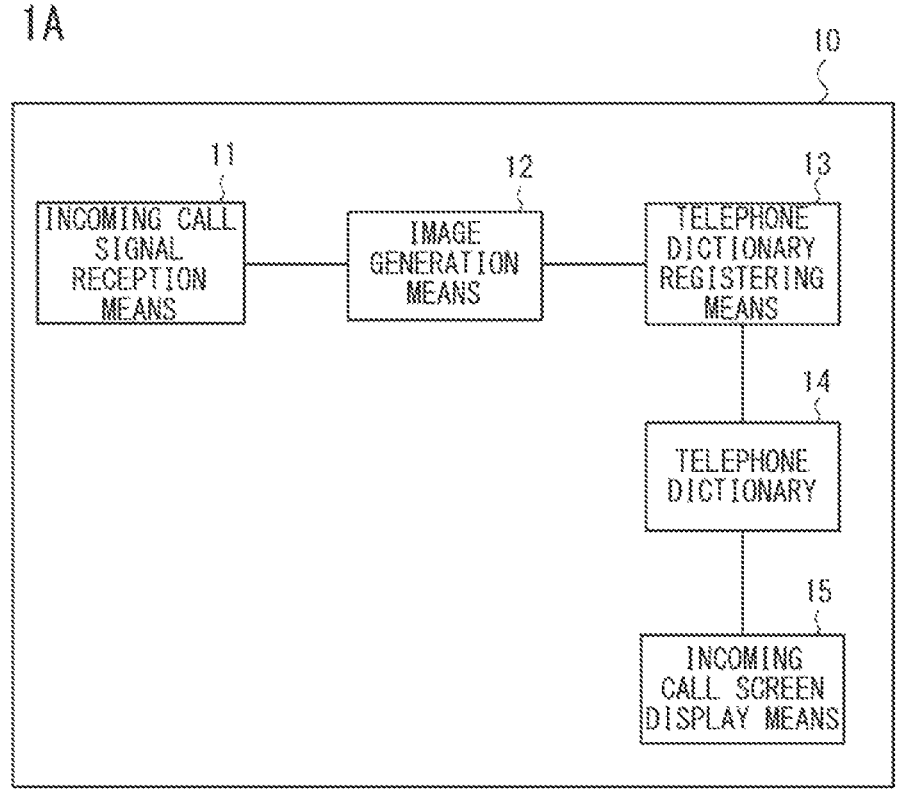
FIG. 1A is a block diagram showing a schematic configuration of a terminal device according to the present disclosure in one aspect.

Prior to escribing embodiments of the present disclosure, an outline of the present disclosure will be described. FIG. 1A shows a schematic configuration of a portable terminal device according to the present disclosure in one aspect. A portable terminal device 10 includes an incoming call signal reception means 11, an image generation means 12, a telephone directory registering means 13, and an incoming call screen display means 15. The incoming call signal reception means 11 receives an incoming call signal when there is a telephone incoming call. The incoming call signal includes a caller number, caller information, and ring type information.

The image generation means 12 generates a caller information image based on the incoming call signal received by the incoming call signal reception means 11. The caller information image is an image including at least a portion of the caller information included in the incoming call signal as character information. The telephone directory registering means 13 generates caller text information based on at least one of the caller information and the ring type information included in the incoming call signal. The telephone directory registering means 13 registers the caller number included in the incoming call signal, the caller text information and the caller information image in a telephone directory 14 managed in the portable terminal device 10.

The incoming call screen display means 15 receives a caller number, and acquires caller text information and a caller information image registered corresponding to the received caller number from the telephone directory 14. The incoming call screen display means 15 displays an incoming call screen including the caller text information and the caller information image on the display screen of the portable terminal device to inform the user of the incoming call.

According to the present disclosure, the image generation means 12 generates the caller information image based on the incoming call signal. The telephone directory registering means 13 registers the caller text information and the caller information image in the telephone directory 14. The incoming call screen display means 15 displays the caller text information and the caller information image on an incoming call screen. In the present disclosure, the information of the caller is displayed on the incoming call screen as image information. For example, when the portable terminal device 10 is used as a nurse call receiving terminal in a nurse call system, the combination of the caller number and the caller can be frequently changed. According to the present disclosure, even in such a situation, the information of the caller and the like can be displayed as image information when an incoming call is received, and the user who receives the incoming call can easily know who the incoming call is from.

Specifically, a case is considered in which the portable terminal device 10 is used as a nurse call receiving terminal, and iPhone manufactured by Apple is used for the portable terminal device 10. When the nurse call terminal is not used for telephone conversations or the like, the nurse call terminal is applied to a security lock so that others cannot use it without permission. When the incoming nurse call is received during the security lock, nurse call applications must use CallKit to respond to incoming nurse calls without unlocking the security lock. In FIG. 1A, functions of the incoming call screen display means 15 corresponds to, for example, a portion of the functions provided by CallKit.

CallKit retrieves information stored in the telephone dictionary and displays the incoming call screen. Accordingly, in order to display information such as the name of the patient who made the nurse call on the nurse call receiving terminal, it is necessary to register the "caller number" and the "patient name" of the nurse call extension unit in the telephone directory application (Contacts) under the OS. "Contacts" correspond to the telephone directory 14 shown in FIG. 1A. However, the patient's room (bed) may be change frequently. In order to display the patient name on the nurse call receiving terminal, it is necessary to update the "caller number" and "patient name" registered in the "Contacts" of all nurse call receiving terminals carried by the medical workers each time the name is changed. In the present disclosure, the caller information image is generated using the caller information included in the incoming call signal, and is registered in the telephone directory 14. Thus, information such as a patient name can be displayed on the nurse call receiving terminal without updating the "caller number" and "patient name" registered in the "Contacts" of all nurse call receiving terminals carried by the medical workers.

Figure 1B:
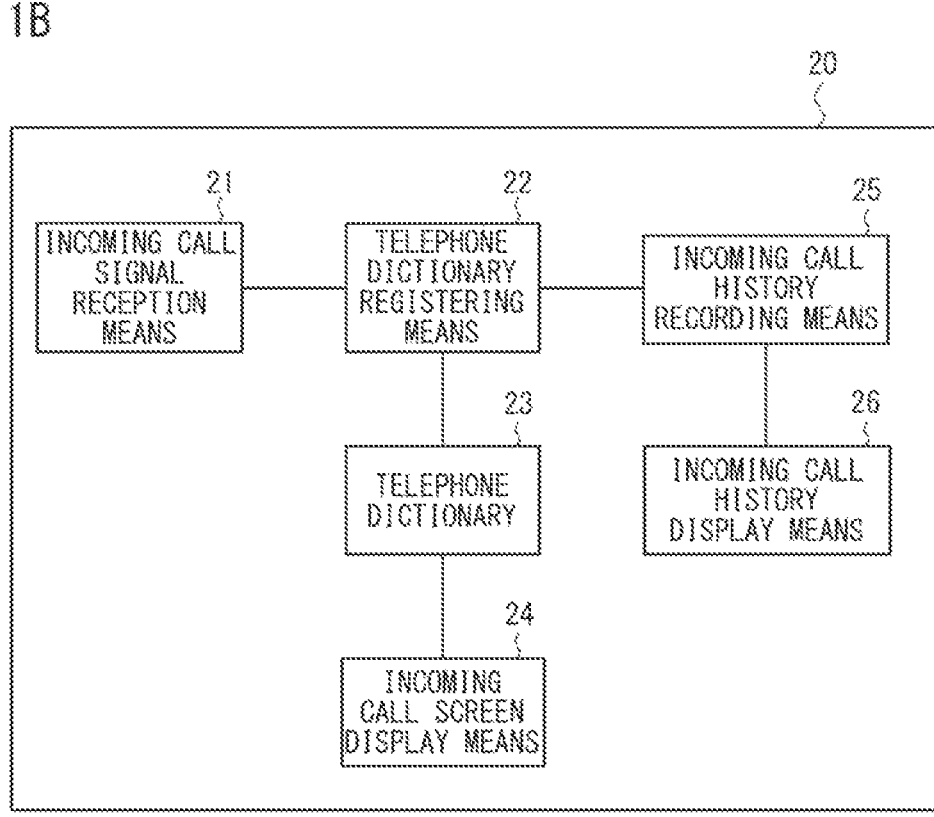
FIG. 1B is a block diagram showing a schematic configuration of a portable terminal device according to the present disclosure in another aspect.

FIG. 1B shows a schematic configuration of a portable terminal device according to the present disclosure in another aspect. A portable terminal device 20 includes an incoming call signal reception means 21, a telephone directory registering means 22, an incoming call screen displaying means 24, an incoming call history recording means 25, and an incoming call history displaying means 26. The incoming call signal reception means 21 receives an incoming call signal when there is a telephone incoming call. The incoming call signal includes a caller number, caller information, and ring type information.

The telephone directory registering means 22 generates caller text information based on at least one of the caller information and the ring type information included in the incoming call signal. The telephone directory registering means 22 registers the caller number included in the incoming call signal and the generated caller text information in a telephone directory 23 managed in the portable terminal device 20.

The incoming call screen display means 24 receives a caller number and acquires caller text information registered corresponding to the received caller number from the telephone directory 23. The incoming call screen display means 24 displays an incoming call screen including the caller text information on the display screen of the portable terminal device to inform the user of the incoming call.

The incoming call history recording means 25 associates the caller number which is a source of a call with the caller text information and records them in incoming call history information. The telephone directory registering means 22 deletes the registered caller number from the telephone directory after the incoming telephone call ends. The incoming call history display means 26 displays an incoming call history including a number of the incoming telephone call and a name of the caller. The incoming call history display means 26 acquires caller text information from the incoming call history information, and displays the acquired caller text information as a name of the caller when displaying the incoming call history.

According to the present disclosure, the telephone directory registering means 22 generates caller text information based on at least one of the caller information and the ring type information included in the incoming call signal, and registers the caller text information in the telephone directory 23. The incoming call screen display means 24 displays caller text information on an incoming call screen. For example, when the portable terminal device 20 is used as a nurse call receiving terminal in a nurse call system, the combination of the caller number and the caller can be frequently changed. According to the present disclosure, even in such a situation, the information of the caller and the like can be displayed when an incoming call is received, and the user who receives the incoming call can easily know who the incoming call is from.

Further, according to the present disclosure, the telephone directory registering unit 22 deletes the registered caller number from the telephone directory 23 after the incoming telephone call ends. When the incoming call history is displayed, the incoming call history display means 26 acquires, from the incoming call history information, the caller text information registered by the incoming call history registering means 25. The incoming call history display means 26 displays the acquired caller text information as the name of the caller. In this way, in the present disclosure, when the incoming call history is displayed, the information of the caller is acquired from the incoming call history information, not the information registered in the telephone directory. Thus, even in a situation where the combination of the caller number and the caller can be changed, information of the caller at the time of the incoming call can be correctly displayed in the incoming call history, while enabling information of the caller and the like to be displayed when an incoming call is received.

Specifically, a case is considered in which the portable terminal device 20 is used as a nurse call receiving terminal, and iPhone manufactured by Apple is used for the portable terminal device 20. When the nurse call terminal is not used for telephone conversations or the like, the nurse call terminal is applied to a security lock so that others cannot use it without permission. When an incoming nurse call is received during the security lock, the nurse call application must use CallKit to respond to the incoming nurse call without unlocking the security lock. In FIG. 1B, functions of the incoming call screen display means 24 corresponds to, for example, a portion of the functions provided by CallKit.

CallKit retrieves information stored in the telephone dictionary and displays the incoming call screen. Accordingly, in order to display information such as the name of the patient who made the nurse call on the nurse call receiving terminal, it is necessary to register the "caller number" and the "patient name" of the nurse call extension unit in the telephone directory application (Contacts) under the OS. "Contacts" corresponds to the telephone directory 23 shown in FIG. 1B. However, the patient's room (bed) may be changed frequently. In order to display the patient name on the nurse call receiving terminal, it is necessary to update the "caller number" and "patient name" registered in the "Contacts" of all nurse call receiving terminals carried by the medical workers each time the name is changed. In the present disclosure, the caller text information is generated using the caller information included in the incoming call signal, and is registered in the telephone directory 23. Thus, information such as a patient name can be displayed on the nurse call receiving terminal without updating the "caller number" and "patient name" registered in the "Contacts" of all nurse call receiving terminals carried by the medical workers.

The incoming call history (call history) information of the OS of iPhone has a restriction that, when the registered name registered in the telephone directory is changed, the display name of the past incoming call history stored in the history is also changed. For example, it is assumed that the called number "1000" corresponds to the patient name "Tanaka" at a certain time point in the past. Thereafter, it is assumed that the patient name corresponding to the caller number "1000" is changed to "Suzuki" due to the change of the hospital room, etc. When Mr./Ms. Suzuki calls the nurse call, a telephone directory registering means 22 registers the caller number "1000" and the patient name "Suzuki" in a telephone directory 23 in association with each other. In this case, when the incoming call history is displayed, the display name of the incoming call history of the nurse call made by Mr./Ms. Tanaka in the past changes to "Suzuki". In this way, when the name (registered name) registered in the telephone directory is changed in iPhone, the display name of the past incoming call history stored in the history is also changed in association with the change. In that case, it would look as if the nurse call was made by Mr./Ms. Suzuki, even though it was Mr./Ms. Tanaka who made the nurse call in the past.

For the above problem, in the present disclosure, the telephone directory registering unit 22 deletes the registered caller number from the telephone directory 23 after a call ends. By doing so, in the telephone directory 23, the correspondence between the caller number and the registered name (caller text information) is canceled. As for storing the incoming call history information, the incoming call history recording means 25 registers the caller text information in the incoming call history information using, for example, 'LocalizeCallerName'. The incoming call history display means 26 displays the caller text information registered in 'LocalizeCallerName' in the incoming call history information. Thus, even if the name registered for the same number in the telephone directory 23 is changed, the name of the caller at the time of the incoming call can be displayed in the incoming call history.

Figure 2:
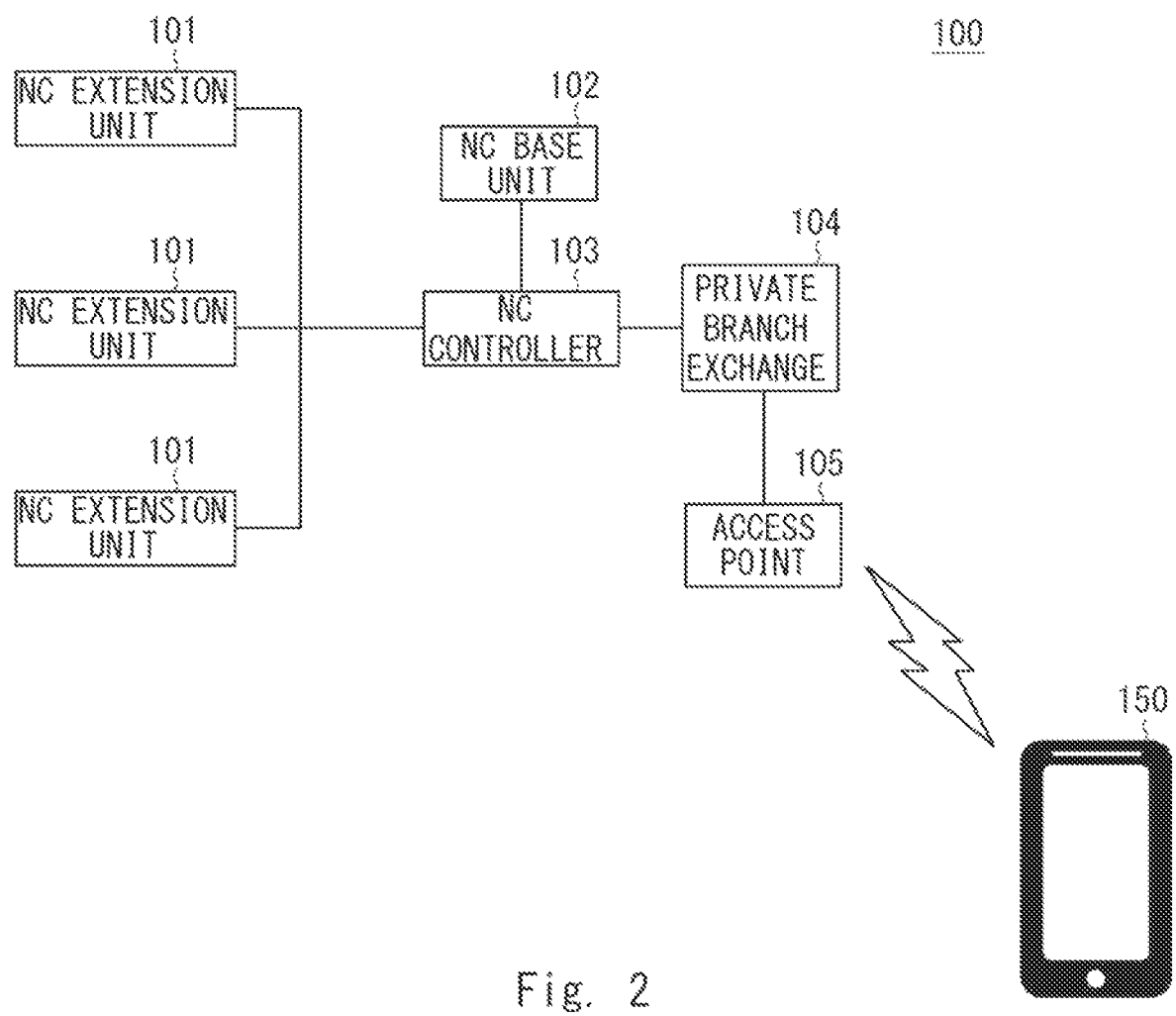
FIG. 2 is a block diagram showing a telephone system including a portable terminal device according to a first embodiment of the present disclosure.

Hereinafter, embodiments of the present disclosure will be described with reference to the drawings. FIG. 2 shows a telephone system according to a first embodiment of the present disclosure. In the present embodiment, the telephone system is configured as a Nurse Call (NC) system. The NC system 100 includes NC extension units 101, an NC base unit 102, an NC controller 103, a private branch exchange 104, an access point 105, and a portable terminal device 150.

The NC extension unit 101 is a device used when a patient calls a medical worker. The NC extension unit 101 includes a call button, a speaker, a microphone, and the like. The NC extension unit 101 is arranged, for example, in a hospital room, each bed in the hospital room, a bathroom, a toilet, or the like. The NC extension unit 101 transmits a call signal to the nurse call controller 103 when the patient presses the call button. It should be noted that, although three NC extension units 101 are shown in FIG. 2, the present disclosure is not limited thereto. The NC system 100 may include any number of NC extension units 101.

The NC base unit 102 is installed at a nurse station or the like, and is configured to respond to a call from the NC extension unit 101. The nurse call base unit 102 includes, for example, a handset for responding to a call, a small monitor for displaying patient information, and a large monitor for displaying detailed information about each patient as list. The NC extension unit 101 and the NC base unit 102 may be the same as the NC extension unit and the NC base unit used in a common NC system.

The private branch exchange 104 is a device for managing the call connection between the NC extension unit 101 and the portable terminal device 150 and the call connection between the NC base unit 102 and the portable terminal device 150. The private branch exchange 104 is installed, for example, in a hospital. The access point 105 is connected to the private branch exchange 104 by wired communication and is connected to the portable terminal device 150 by wireless communication. The access point 105 includes a wireless transceiver, an antenna, and the like. The access point 105 are arranged, for example, at various places in the hospital. The portable terminal device 150 is registered in the private branch exchange 104, and can transmit and receive a signal to and from the private branch exchange 104 through the access point 105.

The NC controller 103 controls communication between the NC extension unit 101 and each device. For example, when a nurse call is transmitted from the NC extension unit 101, the NC controller 103 controls communication between the NC extension unit 101 and the NC base unit 102. Further, the NC controller 103 controls communication between the NC extension unit 101 and the portable terminal device 150. The NC controller 103 may be integrated with the NC base unit 102.

The NC controller 103 manages places where the NC extension units 101 are arranged. When the NC extension unit 101 is arranged at the bedside, the NC controller 103 manages which patient uses the NC extension unit 101. When a nurse call is made from an NC extension unit 101, the NC controller 103 identifies which NC extension unit 101 has made the call. Further, the NC controller 103 identifies the name of the patient (caller name) who made the nurse call and where the nurse call was made from.

When a nurse call is made, the NC controller 103 transmits an incoming call signal including a caller number (extension number), patient information (caller information), and ring type information to the portable terminal device 150. The portable terminal device 150 receives the incoming call signal through the private branch exchange 104 and the access point 105.

The patient information includes, for example, at least one of a patient name and information indicating the location where the nurse call is made from. The patient information may alternatively or additionally include information indicating a medical specialty of a patient. The ring type information includes information indicating that the call is for a nurse call (incoming nurse call). The NC controller 103 may change the ring type information according to the urgency of the nurse call. The NC controller 103 may determine the urgency of the nurse call based on, for example, the medical specialty of a patient and/or the location of the NC extension unit 101.

Figure 3:
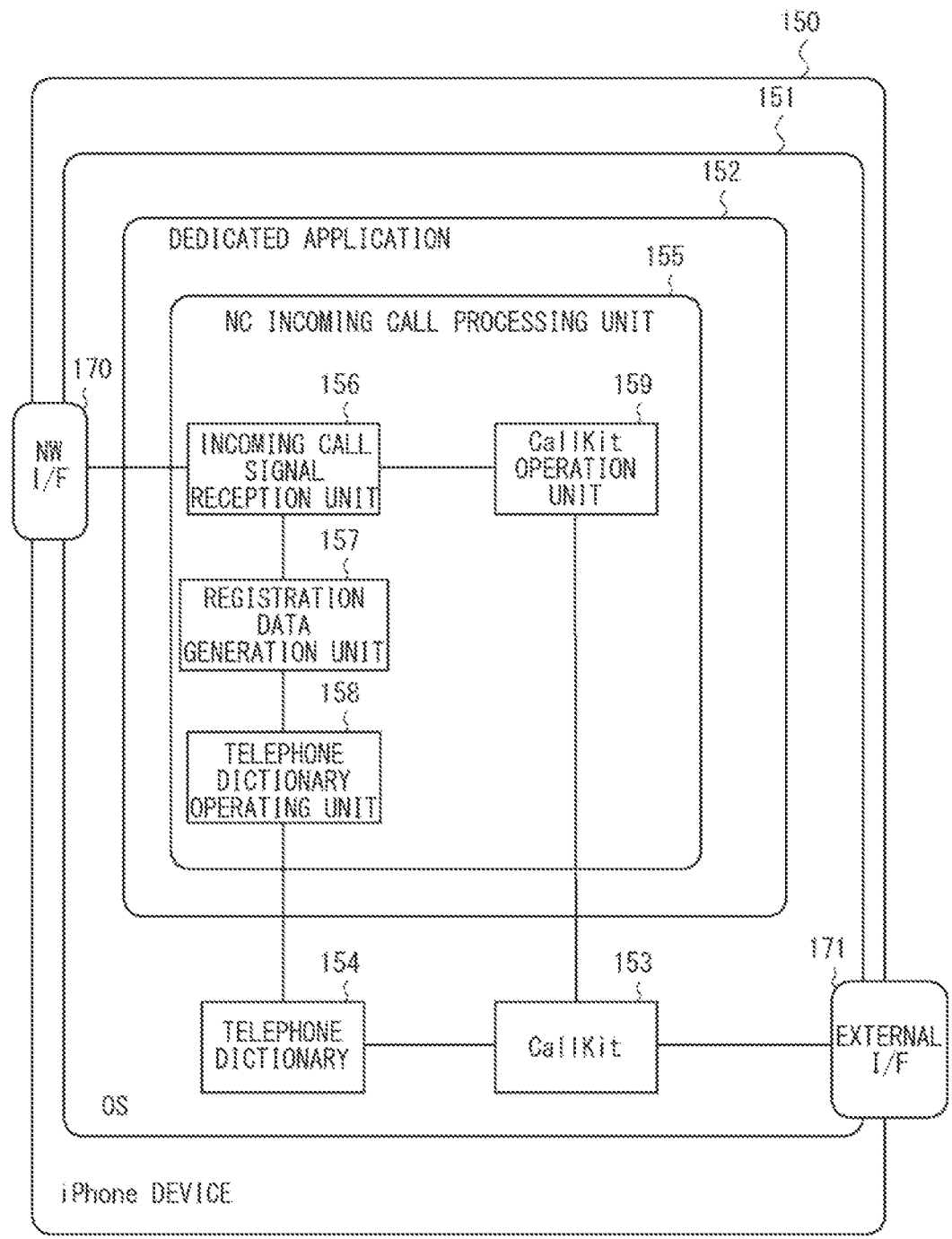
FIG. 3 is a block diagram showing a logical configuration of a portable terminal device.

FIG. 3 shows a logical configuration of the portable terminal device 150. It is assumed that the portable terminal device 150 is an iPhone device manufactured by Apple. A VoIP application (hereinafter also referred to as a dedicated application) 152 supporting an incoming nurse call is installed in the portable terminal device 150. In the portable terminal device 150, the dedicated application 152, CallKit 153 and the telephone directory 154 operate on an OS 151. The portable terminal device 150 corresponds to the portable terminal device 10 shown in FIG. 1A.

The dedicated application 152 includes an NC incoming call processing unit 155. The NC incoming call processing unit 155 includes an incoming call signal reception unit 156, a registration data generation unit 157, a telephone directory operating unit 158, and a CallKit operating unit 159. It should be noted that the dedicated application 152 also includes other functions (processing unit) such as a function for calling the NC extension unit 101 and the NC base unit 102, although they are not shown in the drawing.

The incoming call signal reception unit 156 receives the incoming call signal transmitted from the NC controller 103 via the network interface (NW I/F) 170. When the incoming call signal is the incoming call signal of the nurse call, the incoming call signal reception unit 156 sends, to the registration data generation unit 157, the caller number, the patient information, and the ring type information included in the incoming call signal. The incoming call signal reception unit 156 corresponds to the incoming call signal reception means 11 shown FIG. 1A.

The registration data generation unit 157 generates registration data to be registered in the telephone directory 154 based on the information received from the incoming call signal reception unit 156. Generating the registration data includes generating a patient information image (caller information image). The registration data generation unit 157 generates an image, as the patient information image, including at least a portion of patient information included in the incoming call signal as character information. The registration data generation unit 157 includes means corresponding to the image generation means 12 shown in FIG. 1A.

The registration data generation unit 157 may change the feature of the patient information image, for example, in accordance with the ring type information included in the incoming call signal. For example, the registration data generation unit 157 may generate a patient information image in a display color in accordance with the ring type information. For example, when the ring type information indicates that the urgency is low, the registration data generation unit 157 generates a patient information image, the background color of which is black. When the ring type information indicates that the urgency is high, the registration data generation unit 157 generates a patient information image, the background color of which is red. By doing so, the user who receives the nurse call can determine the degree of urgency based on the color of the image.

The telephone directory operating unit 158 operates registration data of the telephone directory (Contacts) 154. In the telephone dictionary 154, a set of a number, a name and an image can be registered. Further, in the telephone directory 154, a ringtone can be individually set to each telephone directory data. The telephone directory operating unit 158 generates a text (caller text information) representing a name to be registered in the telephone directory based on at least one of the patient information and the ring type information. The telephone directory operating unit 158 refers to, for example, the patient information, and generates text information representing at least one of the patient name and the place where the nurse call made from as the caller text information. Alternatively, the telephone directory operating unit 158 may generate text information indicating the degree of urgency as the caller information with reference to the ring type information. The telephone directory operating unit 158 may generate text information in which the text information representing a patient name or the like and the text information representing urgency are combined as the caller text information.

The telephone directory operating unit 158 registers a caller number included in the incoming call signal in "number" of the telephone directory data. The telephone directory operating unit 158 registers the caller text information (string) generated based on at least one of the patient information and the ring type information in "name" of the telephone directory data. The telephone directory operating unit 158 registers the patient information image generated by the registration data generation unit 157 in "image" of the telephone directory data. The telephone directory operating unit 158 corresponds to the telephone directory registration means 13 shown in FIG. 1A.

The telephone directory operating unit 158 registers a plurality of templates of telephone directory data in the telephone directory 154, for example, when the dedicated application 152 is started up for the first time. At this time, the telephone directory operating unit 158 registers a plurality of templates corresponding to each ring type information in the telephone directory 154. The user sets the ringtone for each template by using a telephone dictionary application. The user can specify a sound source implemented in the portable terminal device 150 when setting the ringtone. "Sound source implemented in the portable terminal device 150" refers to, for example, a sound source selectable as "ringtone" on an iPhone device. The user sets a ringtone for each template, whereby a ringtone is individually set to each template.

Figures 4, 5:
FIG. 4 is a diagram showing an example of ringtone settings.
FIG. 5 is a diagram showing an example of an incoming call screen.

FIG. 4 shows an example of the ringtone setting. In this example, it is assumed that a template registered in the telephone dictionary 154 as telephone dictionary data of No. 1 corresponds to a template corresponding to ring type information "1". It is assumed that a template registered as telephone dictionary data of No. 2 corresponds to a template corresponding to ring type information "2". It is assumed that a template registered as telephone dictionary data of No. 3 corresponds to a template corresponding to ring type information "3". For example, the user sets "ringtone A" as the ringtone of the template corresponding to the ring type information "1". The user sets "ringtone B" as the ringtone of the template corresponding to the ring type information "2", and sets "ringtone C" as the ringtone of the template corresponding to the ring type information "3". It should be noted that the setting of the ringtone includes setting of the incoming call notification using a vibrator which does not actually sound.

The telephone directory operating unit 158 selects a template corresponding to the ring type information included in the incoming call signal from a plurality of templates, and registers the caller number, the caller text information and the patient information image in the selected template. For example, when the ring type information is "1", the telephone directory operating unit 158 selects the template registered as the telephone dictionary data of No. 1. The telephone dictionary operating unit 158 registers the caller number, the caller text information and the patient information image in the telephone directory data of No. 1. When the ring type information is "3", the telephone directory operating unit 158 selects the template registered as the telephone dictionary data of No. 3. In this case, the telephone directory operating unit 158 registers the caller number, the caller text information and the patient information image in the telephone directory data of No. 3. After the incoming nurse call ends, the telephone directory operating unit 158 may delete the registered information from the template in the telephone directory 154. In this case, the template is initialized after the call ends.

The CallKit operating unit 159 notifies the CallKit 153 of the caller number and an incoming call after the telephone dictionary operating unit 158 registers information in the telephone dictionary 154. The CallKit 153 is a framework that provides, in the OS 151, a function for managing conflict between applications using the call function, a function for enabling an incoming call during a security lock, and a function for displaying an incoming screen. When an incoming call is notified, the CallKit 153 acquires the caller text information registered corresponding to the caller number and the caller image (patient information image) from the telephone directory 154. Further, a ringtone set for the caller number is acquired. The CallKit 153 displays an incoming call screen including the acquired caller text information and the patient information image on the display screen through an external interface (external I/F) 171. The CallKit 153 outputs the acquired ringtone from a speaker through an external I/F 171.

FIG. 5 shows a display example of the incoming call screen. In an incoming call screen 200, an area 201 is an area in which information (string) registered in "name" in the telephone directory 154 is displayed. The telephone directory operating unit 158 generates a character string in which, for example, a character string "nurse call", a bed number where a nurse call has been made from, a patient name, and the like are combined as the caller text information. The telephone directory operating unit 158 registers the generated caller text information in the "name" of the telephone directory 154. If the number of characters of the caller text information exceeds the number of characters that can be displayed in the area 201, the caller text information is scrolled and displayed in the area 201.

In the incoming call screen 200, an area 202 is an area in which an image registered as the caller image in the telephone directory 154 is displayed. The registration data generation unit 157 generates an image including a character string obtained by combining a character string "nurse call", a bed number where a nurse call has been made from, a patient name, and an extension number as the patient information image. The registration data generation unit 157 changes the background color in accordance with the ring type information in the generation of the patient information image. For example, the registration data generation unit 157 sets the background color of the patient information image to red when the ring type information indicates "high" urgency. The registration data generation unit 157 sets the background color of the patient information image to black when the ring type information indicates "low" urgency. The telephone directory operating unit 158 registers the patient information image generated by the registration data generation unit 157 in "image" of the telephone directory 154.

Figure 6:
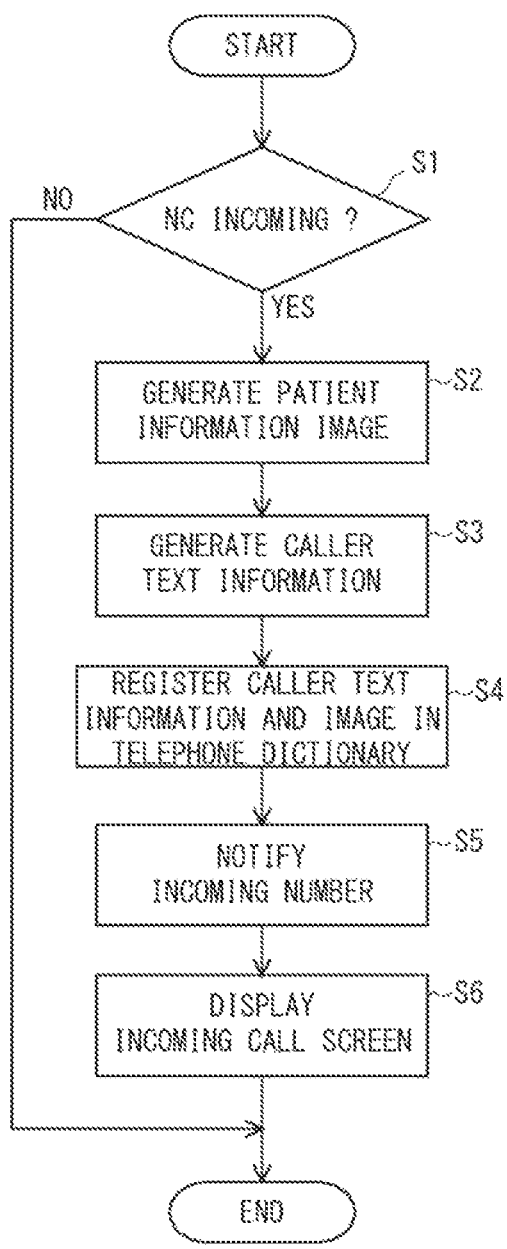
FIG. 6 is a flowchart showing an operation procedure when a nurse call is received.

Next, an operation procedure will be described. FIG. 6 shows an operation procedure (incoming call screen display method) in the portable terminal device 150 when a nurse call is received. When the call button of the NC extension unit 101 is operated, the NC controller 103 identifies the caller number, the patient information, and the ring type information, and transmits the information on them to the private branch exchange 104. The private branch exchange 104 transmits an incoming call signal including the caller number, the patient information, and the ring type information as accompanying data to the portable terminal device 150 via the access point 105.

The dedicated application 152 in the portable terminal device 150 receives an incoming call signal. The incoming call signal reception unit 156 of the NC incoming call processing unit 155 in the dedicated application 152 determines whether or not the incoming call signal indicates an incoming nurse call (Step S1). In step S1, the incoming call signal reception unit 156 determines whether or not the incoming call signal indicates an incoming nurse call based on the ring type information included in the incoming call signal. When the incoming call signal reception unit 156 determines that the incoming call signal does not indicate the incoming nurse call, the processing ends.

When the incoming call signal reception unit 156 determines in step S1 that the incoming call signal indicates the incoming nurse call, the incoming call signal reception unit 156 sends the caller number, the patient information, and the ring type information to the registration data generation unit 157. The registration data generation unit 157 generates a patient information image based on the caller number, the patient information, and the ring type information (Step S2). In step S2, the registration data generation unit 157 generates, for example, an image in which the caller number and the patient information to be displayed are embedded as the patient information image. In the generation of the patient information image, the registration data generation unit 157 may change the characteristics of the image, such as the display color, according to the ring type information. In this case, the user can easily distinguish the ringing type visually.

The telephone directory operating unit 158 generates caller text information based on at least one of the patient information and the ring type information (Step S3). In step S3, the telephone directory operating unit 158 generates, for example, data (string) obtained by combining the patient name and the urgency level as the caller text information. The telephone directory operating unit 158 may include the caller number in the caller text information.

The telephone directory operating unit 158 associates the patient information image generated in step S2 and the caller text information generated in step S3 with the caller number and registered them in the telephone directory 154 (Step S4). In step S4, the telephone directory operating unit 158 selects a template corresponding to the ring type information included in the incoming call signal from among the plurality of templates. The telephone directory operating unit 158 registers the caller text information in "name" of the selected template, and registers the patient information image in "image".

The CallKit operating unit 159 notifies the CallKit 153 of the caller number after the registration in the telephone dictionary 154 is completed (Step S5). The CallKit 153 acquires data of "name" and "image" corresponding to the notified incoming call number from the telephone directory 154, and displays an incoming call screen (Step S6). In step S6, the CallKit 153 acquires the caller text information and the patient information image registered in step S4 from the telephone directory 154, and displays them on the incoming call screen (See FIG. 5). Further, the CallKit 153 acquires a ringtone setting corresponding to the telephone dictionary data (See also FIG. 4). The CallKit 153 sounds a ringtone for the incoming calls set in the ringtone settings.

According to the present embodiment, the registration data generation unit 157 generates a patient information image to be registered in the telephone directory 154 based on the patient information included in the incoming call signal. The telephone directory operating unit 158 generates caller text information and registers the caller text information and the patient information image in the telephone directory 154. The CallKit 153 acquires the caller text information and the patient information image from the telephone directory 154, and displays the caller text information and the patient information image on an incoming call screen. In this way, patient information can be displayed on the incoming call screen for the nurse call while using the CallKit 153. In the present embodiment, even in a system in which a combination of information such as a caller number and a patient name is frequently changed, the information displayed on the incoming call screen can be dynamically changed without updating the registration information in all terminals.

In the incoming call screen 200 (See FIG. 5), although the caller text information is displayed in the area 201, characters that can be displayed in the area 201 are limited. In present embodiment, the patient information is displayed as image information in the area 202 on the incoming call screen 200. Thus, more information can be presented to the user. For example, in the present embodiment, even when the amount of information in the patient information image is large, the information can be displayed on the incoming call screen without scrolling. Therefore, the user can obtain the desired information without waiting for the end of the scroll. Further, in the present embodiment, the display color of the patient information image displayed in the area 202 can be changed according to the ring type information. In this case, the user can recognize, by the display color, which ring type information the incoming nurse call corresponds to.

In the present embodiment, templates each corresponding to the ring type information are prepared in the telephone directory 154. In the telephone directory 154, a ringtone can be individually set to each template. The telephone directory operating unit 158 registers the caller text information and the patient information image in a template corresponding to the ring type information included in the incoming call signal. The CallKit 153 has a restriction that when the system ringtone of an iPhone device is used as a VoIP ringtone, only the ringtone set in the telephone dictionary data in association with the caller number can be sounded. In the present embodiment, as described above, receiving incoming calls using the CallKit 153 can be realized, and switching ringtones according to the ring type information can be realized.

Figure 7:
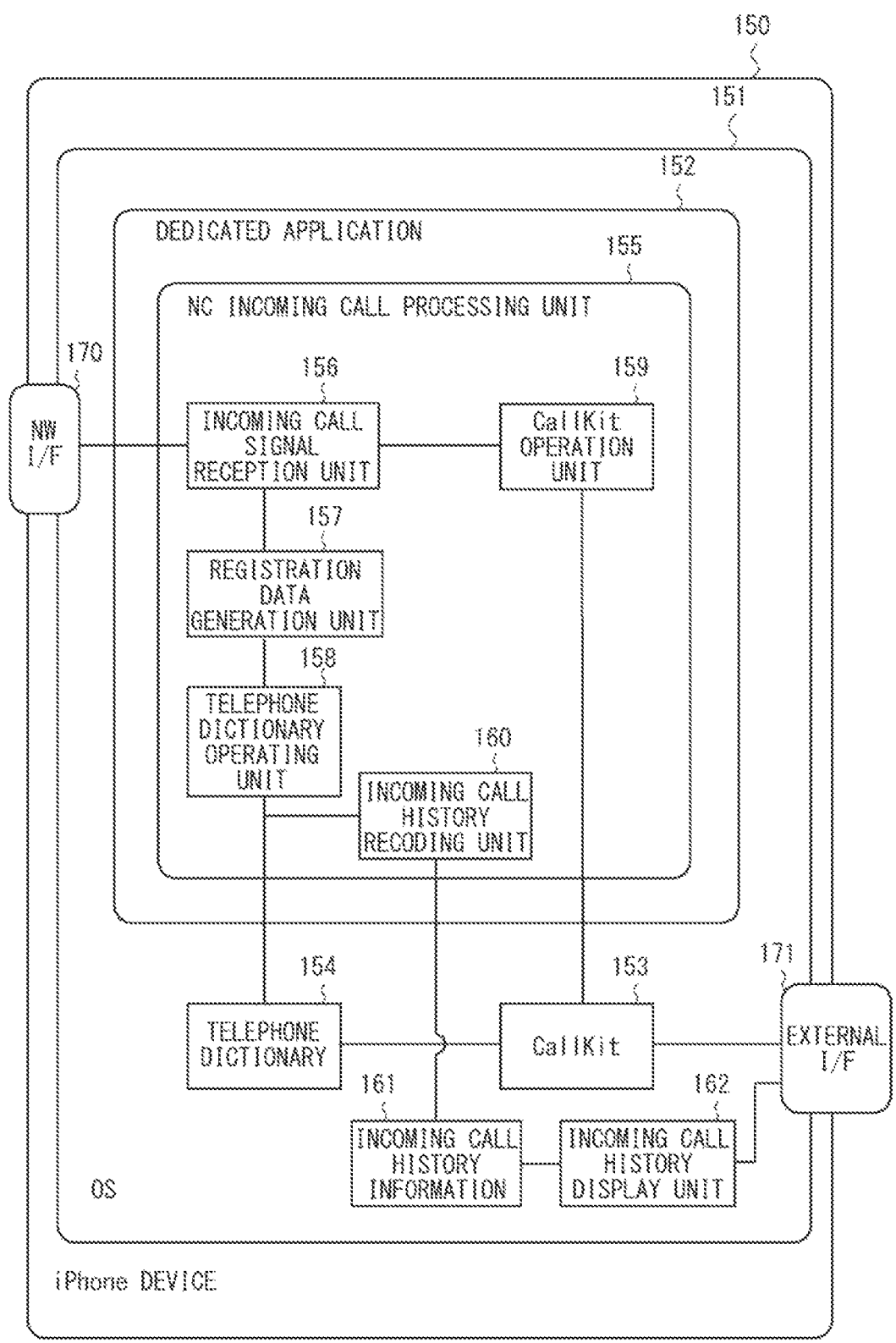
FIG. 7 is a block diagram showing a logical configuration of a portable terminal device according to a second embodiment of the present disclosure.

Next, a second embodiment of the present disclosure will be described. FIG. 7 shows a logical configuration of a portable terminal device according to a second embodiment of the present disclosure. In the present embodiment, it is assumed that the portable terminal device 150 is an iPhone device manufactured by Apple. The portable terminal device 150 includes an incoming call history recording unit 160, incoming call history information 161, and an incoming call history display unit 162 in addition to the logical configuration of the portable terminal device 150 in the first embodiment shown in FIG. 3. The incoming call history recording unit 160 is included in the NC incoming call processing unit 155 included in the dedicated application 152. The incoming call history information 161 and the incoming call history display unit 162 operate on the OS 151.

In the present embodiment, the portable terminal device 150 corresponds to the portable terminal device 20 shown in FIG. 1B. The incoming call signal reception unit 156 corresponds to the incoming call signal reception means 21 shown in FIG. 1B. The telephone directory operating unit 158 corresponds to the telephone directory registration means 22 shown in FIG. 1B. The telephone directory 154 corresponds to the telephone directory 23 shown in FIG. 1B. The incoming call history recording unit 160 corresponds to the incoming call history recording means 25 shown in FIG. 1B. The incoming call history display unit 162 corresponds to the incoming call history display means 26 shown in FIG. 1B. Some of the functions provided by the CallKit 153 include the functions of the incoming screen display means 24 shown in FIG. 1B. The operations of the incoming call signal reception unit 156, the registration data generation unit 157, the CallKit operating unit 159, and the CallKit 153 may be the same as those described in the first embodiment.

In addition to the operation described in the first embodiment, the telephone directory operating unit 158 deletes the registered caller number from the telephone directory 154 after the call ends. The telephone directory operating unit 158 deletes, for example, a record (e.g., a set of a number, a names, and an image) corresponding to the registered caller number from the telephone directory 154, thereby deleting the caller number from the telephone directory 154. Alternatively, the telephone directory operating unit 158 may delete the caller number from the telephone directory 154 by initializing the telephone directory 154.

The incoming call history recording unit 160 associates the caller number with the caller text information generated by the telephone dictionary operating unit 158 and stores them in the incoming call history information 161. The incoming call history information 161 includes, for example, an incoming call number (number of the source of the call), LocalizeCallerName, and an incoming call date and time. The incoming call history recording unit 160 records the caller number in the incoming call number and records the caller text information in LocalizeCallerName. The incoming call history recording unit 160 records the date and time of the incoming call in the incoming call date and time. For example, the incoming call history recording unit 160 records the caller number and the caller text information in the incoming call history information 161 each time the incoming call signal reception unit 156 receives an incoming call signal. The incoming call history information 161 may include not only the incoming call history of the dedicated application 152 but also the incoming call history of other applications in the mobile terminal device 150 such as a telephone application.

The incoming call history display unit 162 displays the incoming call history when the user performs an operation for displaying the incoming call history. The incoming call history display unit 162 displays the incoming call history on a display screen through an external I/F 171. In the present embodiment, it is assumed that the user performs an operation for displaying the incoming call history after the telephone directory operating unit 158 deletes the caller number from the telephone directory 154 after the call ends. The incoming call history display unit 162 acquires caller text information from the incoming call history information 161, and displays the caller text information acquired from the incoming call history information 161 as a name of a caller in the display of the incoming call history.

More specifically, when the user performs an operation for displaying the incoming call history, the incoming call history display unit 162 determines whether or not the incoming call number recorded in the incoming call history information 161 is registered in the telephone directory 154. When the incoming call number is not registered in the telephone directory 154, the incoming call history display unit 162 acquires the caller text information recorded in the LocalizeCallerName from the incoming call history information 161. The incoming call history display unit 162 displays the caller text information acquired from the incoming call history information 161 as the name of the caller. On the other hand, when the incoming call number is registered in the telephone directory 154, the incoming call history display unit 162 acquires name information stored in association with the incoming call number. The incoming call history display unit 162 displays the name information acquired from the telephone directory 154 as the name of the caller.

Here, a case is considered in which the telephone directory operating unit 158 does not delete the caller number from the telephone directory 154 after the call ends, and the incoming call history recording unit 160 does not record the caller text information in LocalizeCallerName. FIG. 8A shows an incoming call history display in a certain situation. In FIG. 8A, "history number" indicates the number for identifying the incoming call history, and "caller number" indicates the number of the source of a call (caller number). "Display name" indicates the name displayed in the incoming call history, and "incoming time" indicates the date and time of the incoming call. In this situation, it is assumed that the caller number "1000" corresponds to "Tanaka". When there is an incoming call from the caller number "1000", the telephone directory operating unit 158 registers the name "Tanaka" corresponding to the number "1000" in the telephone directory 154. The incoming call history display unit 162 acquires the name "Tanaka" from the telephone directory 154 in the display of the incoming call history, and displays "Tanaka" for the incoming call number "1000" in the display of the incoming call history. The user of the portable terminal device 150 can know that the incoming calls of the history numbers "1" and "2" are the incoming calls from "Tanaka" by referring to the incoming call history.

FIG. 8B shows an incoming call history display in another situation. In this situation, for example, a case is considered in which "Tanaka" is discharged from a hospital and a bed (hospital room) which was used by "Tanaka" is used by "Suzuki". In this situation, when there is an incoming call from the caller number "1000", the telephone directory operating unit 158 registers the name "Suzuki" in the telephone directory 154 corresponding to the number "1000". In the display of the incoming call history, the incoming call history display unit 162 acquires the name "Suzuki" from the telephone directory 154, and displays "Suzuki" for the received call number "1000" in the incoming call history. In this case, along with the change of the registered name in the telephone directory 154, not only the display name of the history number "3" becomes "Suzuki" but also the display names of the history numbers "1" and "2" become "Suzuki". In this case, the incoming calls of the history numbers "1" and "2", which are actually the incoming calls from the "Tanaka", are all seen as the incoming calls from "Suzuki" in association with the registered contents of the telephone directory 154.

To solve the above problem, in the present embodiment, the telephone directory operating unit 158 deletes the caller number from the telephone directory 154 after the call. Further, the incoming call history recording unit 160 records the caller text information in LocalizeCallerName in the incoming call history information 161. By doing so, the display of the information recorded in the LocalizeCallerName is enabled in the display of the incoming call history, and the name of the caller at the time of receiving the call can be displayed in the incoming call history.

FIG. 9 shows an incoming call history display in the present embodiment. The incoming call history recording unit 160 records "Tanaka" in the LocalizeCallerName of the incoming call history information 161 when the calls of the history numbers "1" and "2" are received. When the call of the history number "3" is received, the incoming call history recording unit 160 records "Suzuki" in the LocalizeCallerName of the incoming call history information 161.

In the present embodiment, the telephone directory operating unit 158 deletes the caller number in the telephone directory 154 after the call is received (for example, after the call ends). Accordingly, when the user performs an operation for displaying the incoming call history after the incoming call of the history number "3" ends, the information of the caller number "1000" of the incoming call received by the dedicated application 152 is not registered in the telephone directory 154. Therefore, the incoming call history display unit 162 displays the caller text information recorded in LocalizeCallerName in the incoming call history. In this way, with respect to the same called number "1000", "Tanaka" can be displayed in the incoming call history for the history numbers "1" and "2", and "Suzuki" can be displayed in the incoming call history for the history number "3".

Figure 10:
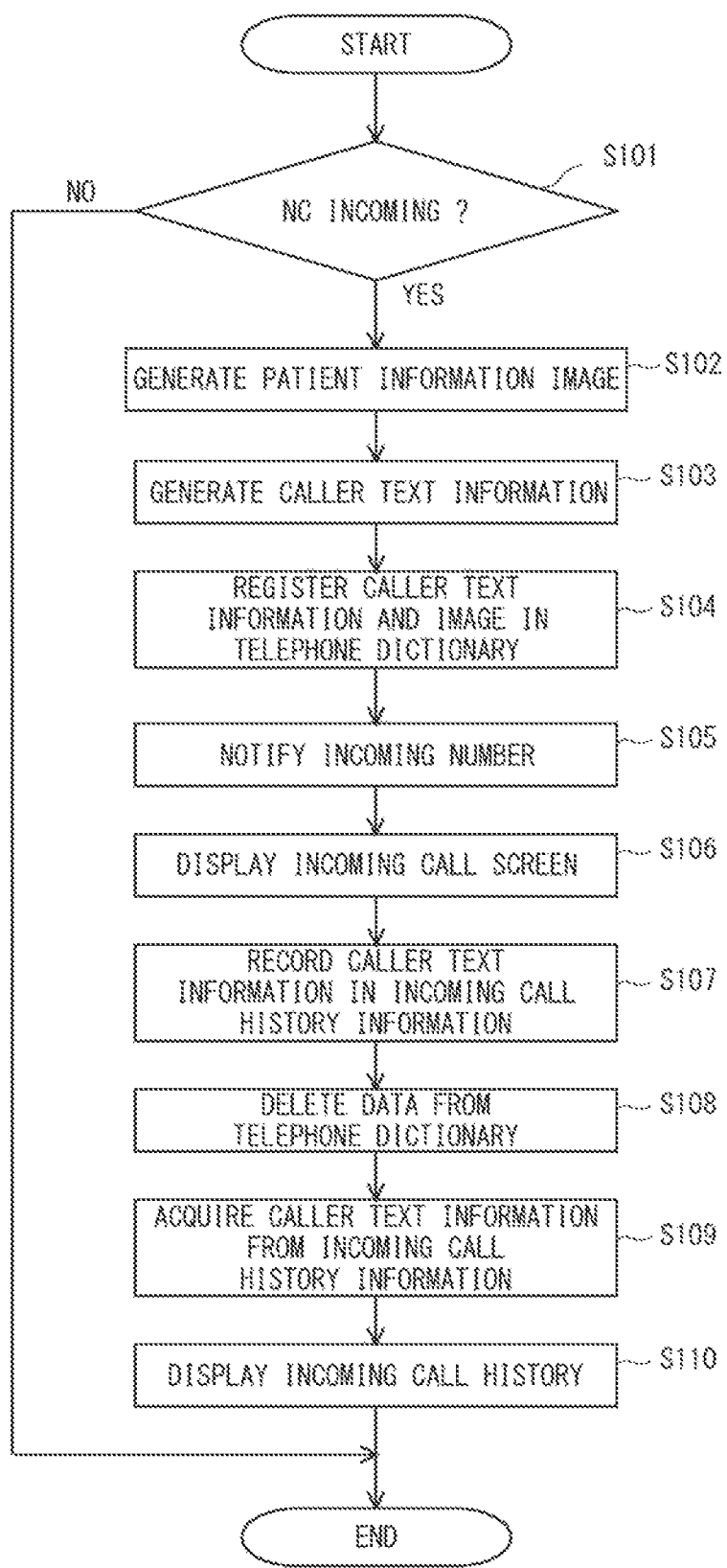
FIG. 10 is a flowchart showing an operation procedure of a portable terminal device.

Next, an operation procedure in the present embodiment will be described. FIG. 10 shows an operation procedure of the portable terminal device 150 including an incoming call history display method. When the call button of the NC extension unit 101 (See FIG. 2) is operated, the NC controller 103 identifies the caller number, the patient information, and the ring type information, and transmits the information on them to the private branch exchange 104. The private branch exchange 104 transmits an incoming call signal including the caller number, the patient information, and the ring type information as accompanying data to the portable terminal device 150 via the access point 105.

The dedicated application 152 in the portable terminal device 150 receives an incoming call signal. The incoming call signal reception unit 156 of the NC incoming call processing unit 155 in the dedicated application 152 determines whether or not the incoming call signal indicates an incoming nurse call (Step S101). In step S101, the incoming call signal reception unit 156 determines whether or not the incoming call signal indicates an incoming nurse call based on the ring type information included in the incoming call signal. When the incoming call signal reception unit 156 determines that the incoming call signal does not indicate the incoming nurse call, the processing ends.

When the incoming call reception unit 156 determines in step S101 that the incoming call signal indicates the nurse call incoming call, the incoming call signal reception unit 156 sends the caller number, the patient information, and the ring type information to the registration data generation unit 157. The registration data generation unit 157 generates a patient information image based on the caller number, the patient information, and the ring type information (Step S102). The telephone directory operating unit 158 generates caller text information based on at least one of the patient information and the ring type information (Step S103). The telephone directory operating unit 158 associates the patient information image generated in step S102 and the caller text information generated in step S103 with the caller number and registers them in the telephone directory 154 (Step S104).

The CallKit operating unit 159 notifies the CallKit 153 of the caller number after the registration in the telephone dictionary 154 is completed (Step S105). The CallKit 153 acquires data of "name" and "image" corresponding to the notified incoming call number from the telephone directory 154, and displays an incoming screen (Step S106). Steps 101 to 106 may be the same as Steps S1 to S6 shown in FIG. 6.

The incoming call history recording unit 160 records caller text information in LocalizeCallerName of the incoming call history information 161 in association with the incoming call number (Step S107). The incoming call history recording unit 160 records, for example, the caller text information generated in step S103 in the LocalizeCallerName. After the call ends, the telephone directory operating unit 158 deletes the caller number from the telephone directory 154 (Step S108). In step S108, the telephone directory operating unit 158 deletes, for example, the caller number, the caller image, and the caller text information registered in Step S104 from the telephone directory 154.

When the user performs an operation for displaying the incoming call history, the incoming call history display unit 162 acquires caller text information from the LocalizeCallerName of the incoming call history information 161 (Step S109). The incoming call history display unit 162 displays the incoming call history including the caller number of the call received by the dedicated application 152 and the caller text information acquired from LocalizeCallerName (Step S110).

According to the present embodiment, the incoming call history recording unit 160 records the caller text information in the LocalizeCallerName of the incoming call history information 161. The telephone directory operating unit 158 deletes the caller number from the telephone directory 154 after the incoming call is received. The data (caller text information) generated when the call is received is recoded in the LocalizeCallerName and the caller number in the telephone dictionary 154 is deleted after the call is received, whereby the display of the information recorded in the LocalizeCallerName is enabled in the display of the incoming call history. In this way, even when the registered contents of the telephone directory 154 are changed at the time of receiving an incoming call with respect to a certain number, the name of the caller at the time of receiving an incoming call can be correctly displayed in the incoming call history. Other advantageous effects are the same as those in the first embodiment.

Figure 11:
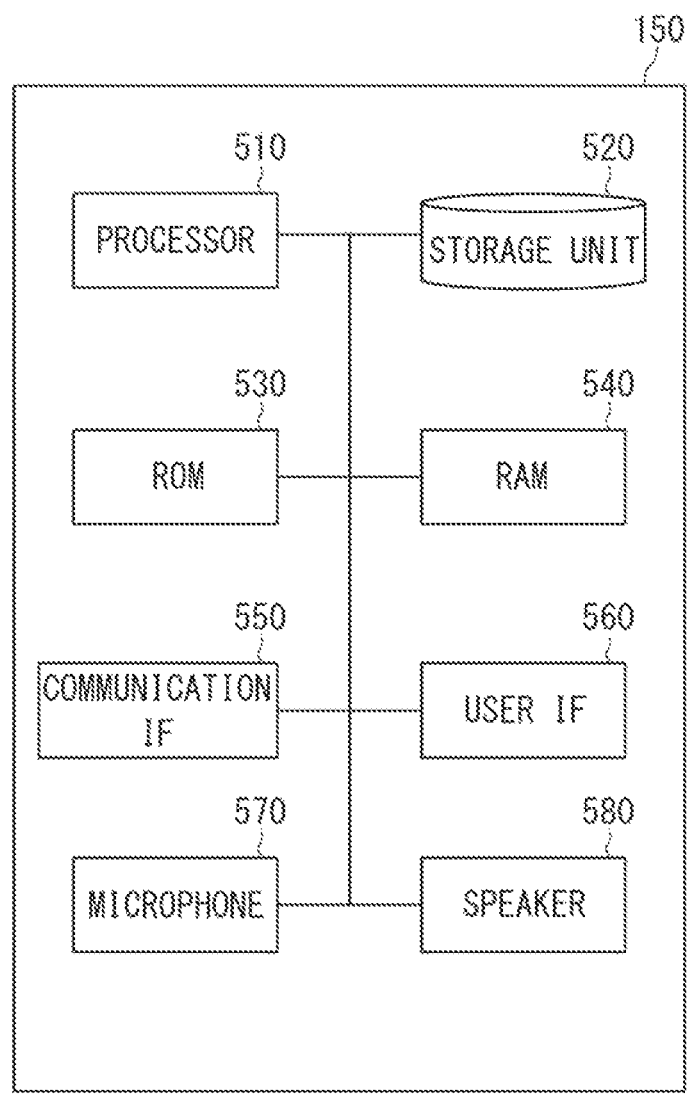
FIG. 11 is a block diagram showing a physical configuration of a portable terminal device.

Next, the physical configuration of the portable terminal device 150 will be described. FIG. 11 shows the physical configuration of the portable terminal device 150. The portable terminal device 150 includes a processor 510, a storage unit 520, a ROM (Read Only Memory) 530, a RAM (Random Access Memory) 540, a communication interface (IF) 550, a user interface 560, a microphone 570, and a speaker 580.

The communication interface 550 is an interface for connecting the access point 105 (See FIG. 2) to the portable terminal device 150 via the wireless communications. The portable terminal device 150 receives the incoming call signal from the private branch exchange 104 via the communication interface 550. The user interface 560 includes, for example, a display device such as a display. The display device is configured as a touch panel and also serves as an input unit. The microphone 570 and the speaker 580 are used in telephone conversation. The speaker 580 is also used for sounding the ringtone.

The storage unit 520 stores various data. The ROM 530 is a nonvolatile memory device. The semiconductor memory device having a relatively small capacity such as a flash memory is used as the ROM 530. The program executed by the processor 510 may be stored in the storage unit 520 or the ROM 530.

The above-described program(s) can be stored and provided to the portable terminal device 150 using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g., magneto-optical disks), optical disk media (such as CDs (compact discs) DVDs (digital versatile disks), etc.), and semiconductor memories (such as mask ROM, PROM (programmable ROM), EPROM (erasable PROM), flash ROM, RAM, etc.). Further, the program(s) may be provided to a computer using any type of transitory computer readable media. Examples of transitory computer readable media include electrical signals, optical signals, and electromagnetic waves. Transitory computer readable media can provide the program(s) to a computer via a wired communication line (e.g., electric wires, and optical fibers) or a wireless communication line.

The RAM 540 is a volatile memory device. For the RAM 540, various semiconductor memory devices such as DRAM (Dynamic Random Access Memory) or SRAM (Static Random Access Memory) are used. The RAM 540 can be used as an internal buffer for temporarily storing data or the like. The processor 510 develops a program stored in the storage unit 520 or the ROM 530 in the RAM 540 and execute the program. The processor 510 executes programs, whereby functions such as the dedicated application 152 and the CallKit 153 shown in FIG. 3 are realized.

It should be noted that, although an example in which the present disclosure is applied to a nurse call is described in each of the above embodiments, the present disclosure is not limited thereto. The present disclosure can be applied to various telephone systems other than nurse calls. Further, in each of the above embodiments, an example in which the incoming call is an incoming call from an extension telephone such as a nurse call is described. However, the present disclosure is not limited to the extension telephone. The present disclosure can be applied to an incoming call from an outside line telephone as long as the caller information is included in the incoming call signal.

In the second embodiment, an example in which the caller text information registered in the telephone directory 154 is the same as the caller text information recorded in the incoming call history information 161 (LocalizeCaller-Name) is described. However, the present disclosure is not limited thereto. In the second embodiment, the name (caller text information) recorded in the incoming call history information 161 may be any information that can identify the caller, and the registered name registered in the telephone directory 154 may be different from the name recorded in the incoming call history information 161.

In the second embodiment, an example in which the registration data generation unit 157 generates a patient information image and the patient information image is displayed on the incoming call screen is described. However, the present disclosure is not limited thereto. For example, the generation of the patient information image may be omitted. In this case, the telephone directory operating unit 158 may register the caller number and the caller text information in the telephone directory 154. Even in this case, since the character string (caller text information) registered in the "name" of the telephone directory 154 is displayed in the area 201 of the incoming call screen 200 (See FIG. 5), the user of the portable terminal device 150 can know to some extent who the incoming call is from.

Although embodiments of the present disclosure have been described in detail, the present disclosure is not limited to the embodiments described above, and changes and modifications made to the embodiments without departing from the spirit of the present disclosure are included in the present disclosure.

For example, all or some of the embodiments disclosed above can be described like in, but not limited to, the following supplementary notes.

[Supplementary Note 1]

A portable terminal device comprising:
incoming call signal reception means for receiving an incoming call signal including a caller number, caller information, and ring type information when an incoming telephone call is received,
image generation means for generating, based on the incoming call signal received by the incoming call signal reception means, a caller information image including at least a portion of the caller information included in the incoming call signal as character information,
telephone dictionary registering means for generating caller text information based on at least one of the caller information and the ring type information, and registering the caller number, the caller text information, and the caller information image in a telephone dictionary managed in the portable terminal device, and
incoming call screen display means for receiving the caller number, acquiring the registered caller text information and the caller information image corresponding to the received caller number from the telephone dictionary, and displaying an incoming call screen including the caller text information and the caller information image.

[Supplementary Note 2]

The portable terminal device according to supplementary note 1, wherein a plurality of telephone dictionary data templates each corresponding to the ring type information are registered in the telephone dictionary,
the telephone dictionary registering means selects a telephone dictionary data template corresponding to the ring type information included in the incoming call signal from the plurality of the telephone dictionary data templates, and registers the caller number, the caller text information, and the caller information image in the selected telephone dictionary data template.

[Supplementary Note 3]

The portable terminal device according to supplementary note 2, wherein a ringtone is individually set for each of the plurality of the telephone dictionary data templates.

[Supplementary Note 4]

The portable terminal device according to supplementary note 2 or 3, wherein the telephone dictionary registering means deletes, from the telephone dictionary data template, the caller number, the caller text information, and the caller information image which the telephone dictionary registering means registered after the incoming telephone call ends.

[Supplementary Note 5]

The portable terminal device according to any one of supplementary notes 1 to 4, wherein the image generation means generates the caller information image in a display color in accordance with the ring type information.

[Supplementary Note 6]

The portable terminal device according to any one of supplementary notes 1 to 5, wherein the caller information includes at least one of a name of a caller and information indicating a location where a call corresponding to the incoming telephone call occurs.

[Supplementary Note 7]

The portable terminal device according to any one of supplementary notes 1 to 5, wherein the incoming telephone call is an incoming call from a nurse call extension unit in a nurse call system, and the caller information includes at least one of a name of a caller, information indicating a location where the nurse call extension unit is placed, and information indicating a medical specialty of the caller.

[Supplementary Note 8]

The portable terminal device according to any one of supplementary notes 1 to 7, wherein functions of the incoming call screen display means are provided as a portion of functions of a frame work providing a function that manages conflict among applications using a call function and a function that enables responding to an incoming call during a security lock.

[Supplementary Note 9]

The portable terminal device according to any one of supplementary notes 1 to 8, further comprising:
  incoming call history recording means for associating the caller number which is a source of a call with the caller text information and storing the caller number and the caller text information in incoming call history information, and
  incoming call history display means for displaying an incoming call history including a number of a source of the incoming telephone call and a name of the source of the incoming telephone call,
  and wherein:
  the telephone dictionary registering means deletes, from the telephone dictionary, the caller number which the telephone dictionary registering means registered after the incoming telephone call ends, and
  the incoming call history display means acquires the caller text information from the incoming call history information and displays the acquired caller text information as a name of the source of a call when displaying the incoming call history.

[Supplementary Note 10]

The portable terminal device according to supplementary note 9, wherein the incoming call history display means is configured to determine whether the number of the source of a call in the incoming call history is registered in the telephone dictionary or not, and acquire, when the number of the source of a call is not registered in the telephone dictionary, the caller text information from the incoming call history information.

[Supplementary Note 11]

The portable terminal device according to supplementary note 10, wherein the incoming call history display means is configured to acquire, when the number of the source of a call is registered in the telephone dictionary, name information stored in association with the number of the source of a call from the telephone dictionary, and display the acquired name information at the name of the source of a call.

[Supplementary Note 12]

The portable terminal device according to any one of supplementary notes 9 to 11, wherein the telephone dictionary registering means deletes the caller number from the telephone dictionary by deleting a record corresponding to the caller number which the telephone dictionary registering means registered from the telephone dictionary.

[Supplementary Note 13]

The portable terminal device according to any one of supplementary notes 9 to 11, wherein the telephone dictionary registering means initializes the telephone dictionary to delete the caller number which the telephone dictionary registering means registered from the telephone dictionary.

[Supplementary Note 14]

A portable terminal device, comprising:
  a processor, and
  a memory,
  wherein the processor is configured to, by executing a program read out from the memory:
  receive an incoming call signal including a caller number, caller information, and ring type information when an incoming telephone call is received, and generate, based on the received incoming call signal, a caller information image including at least a portion of the caller information included in the incoming call signal as character information;
  generate caller text information based on at least one of the caller information and the ring type information;
  register the caller number, the caller text information, and the caller information image in a telephone dictionary managed in the portable terminal device;
  acquire the registered caller text information and the caller information image corresponding to the caller number from the telephone dictionary; and
  display an incoming call screen including the caller text information and the caller information image.

[Supplementary Note 15]

An incoming call screen display method, comprising:
  receiving an incoming call signal including a caller number, caller information, and ring type information when an incoming telephone call is received, and generating, based on the received incoming call signal, a caller information image including at least a portion of the caller information included in the incoming call signal as character information;
  generating caller text information based on at least one of the caller information and the ring type information;
  registering the caller number, the caller text information, and the caller information image in a telephone dictionary managed in the portable terminal device;
  acquiring the caller text information and the registered caller information image corresponding to the caller number from the telephone dictionary; and
  displaying an incoming call screen including the caller text information and the caller information image.

[Supplementary Note 16]

The incoming call screen display method according to supplementary note 15, wherein a telephone dictionary data template corresponding to the ring type information included in the incoming call signal is selected from a plurality of the telephone dictionary data templates registered in the telephone dictionary, and the caller number, the caller text information, and the caller information image are registered in the selected telephone dictionary data template.

[Supplementary Note 17]

The incoming call screen display method according to supplementary note 16, wherein a ringtone is individually set for each of the plurality of the telephone dictionary data templates.

[Supplementary Note 18]

The incoming call screen display method according to supplementary note 16 or 17, wherein the caller number, the caller text information, and the caller information image which are registered in the telephone dictionary are deleted from the telephone dictionary data template after the incoming telephone call ends.

[Supplementary Note 19]

The incoming call screen display method according to any one of supplementary notes 15 to 18, wherein the caller information image is generated in a display color in accordance with the ring type information.

[Supplementary Note 20]

The incoming call screen display method according to any one of supplementary notes 15 to 19, wherein the caller information includes at least one of a name of a caller and information indicating a location where a call corresponding to the incoming telephone call occurs.

[Supplementary Note 21]

The incoming call screen display method according to any one of supplementary notes 15 to 19, wherein the incoming telephone call is an incoming call from a nurse call extension unit in a nurse call system, and the caller information includes at least one of a name of a caller, information indicating a location where the nurse call extension unit is placed, and information indicating a medical specialty of the caller.

[Supplementary Note 22]

A program causing a processor to execute:
receiving an incoming call signal including a caller number, caller information, and ring type information when an incoming telephone call is received, and generating, based on the received incoming call signal, a caller information image including at least a portion of the caller information included in the incoming call signal as character information,
generating caller text information based on at least one of the caller information and the ring type information,
registering the caller number, the caller text information, and the caller information image in a telephone dictionary managed in the portable terminal device, and
causing a frame work, which is configured to acquire information from the telephone dictionary to generate an incoming call screen and display the incoming call screen, to acquire the registered caller text information and the caller information image corresponding to the caller number from the telephone dictionary, and to display an incoming call screen including the caller text information and the caller information image.

[Supplementary Note 23]

The program according to supplementary note 22, causing the processor to execute selecting a telephone dictionary data template corresponding to the ring type information included in the incoming call signal from a plurality of the telephone dictionary data templates registered in the telephone dictionary, and registering the caller number, the caller text information, and the caller information image in the selected telephone dictionary data template.

[Supplementary Note 24]

The program according to supplementary note 23, wherein a ringtone is individually set for each of the plurality of the telephone dictionary data templates.

[Supplementary Note 25]

The program according to supplementary note 23 or 24, causing the processor to execute deleting, after the incoming telephone call ends, the caller number, the caller text information, and the caller information image which are registered from the telephone dictionary data template.

[Supplementary Note 26]

The program according to any one of supplementary notes 22 to 25, the caller information image is generated in a display color in accordance with the ring type information.

[Supplementary Note 27]

The program according to any one of supplementary notes 22 to 26, wherein the caller information includes at least one of a name of a caller and information indicating a location where a call corresponding to the incoming telephone call occurs.

[Supplementary Note 28]

The program according to any one of supplementary notes 22 to 26, wherein the incoming telephone call is an incoming call from a nurse call extension unit in a nurse call system, and
the caller information includes at least one of a name of a caller, information indicating a location where the nurse call extension unit is placed, and information indicating a medical specialty of the caller.

[Supplementary Note 29]

A portable terminal device comprising:
incoming call signal reception means for receiving an incoming call signal including a caller number, caller information, and ring type information when an incoming telephone call is received,
telephone dictionary registering means for generating caller text information based on at least one of the caller information and the ring type information, associating the caller number with the caller text information, and registering the caller number and the caller text information in a telephone dictionary managed in the portable terminal device,
incoming call screen display means for receiving the caller number, acquiring the registered caller text information corresponding to the received caller number from the telephone dictionary, and displaying an incoming call screen including the caller text information,
incoming call history recording means for associating the caller number which is a source of a call with the caller text information and storing the caller number and the caller text information in incoming call history information, and
incoming call history display means for displaying an incoming call history including a number of a source of the incoming telephone call and a name of the source of the incoming telephone call,
and wherein:
the telephone dictionary registering means deletes, after the incoming telephone call ends, the caller number which the telephone dictionary registering means registered from the telephone dictionary, and
the incoming call history display means acquires the caller text information from the incoming call history information and displays the acquired caller text information as a name of the source of a call when displaying the incoming call history.

[Supplementary Note 30]

The portable terminal device according to supplementary note 29, wherein the incoming call history display means is configured to determine whether the number of the source of a call in the incoming call history is registered in the telephone dictionary or not, and acquire, when the number of the source of a call is not registered in the telephone dictionary, the caller text information from the incoming call history information.

[Supplementary Note 31]

The portable terminal device according to supplementary note 30, wherein the incoming call history display means is configured to acquire, when the number of the source of a call is registered in the telephone dictionary, name information stored in association with the number of the source of a call from the telephone dictionary, and display the acquired name information at the name of the source of a call.

[Supplementary Note 32]

The portable terminal device according to any one of supplementary notes 29 to 31, wherein the telephone dictionary registering means deletes the caller number from the telephone dictionary by deleting a record corresponding to the caller number which the telephone dictionary registering means registered from the telephone dictionary.

[Supplementary Note 33]

The portable terminal device according to any one of supplementary notes 29 to 31, wherein the telephone dictionary registering means initializes the telephone dictionary to delete the caller number which the telephone dictionary registering means registered from the telephone dictionary.

[Supplementary Note 34]

The portable terminal device according to any one of supplementary notes 29 to 33, wherein functions of the incoming call screen display means are provided as a portion of functions of a frame work providing a function that manages conflict among applications using a call function and a function that enables responding to an incoming call during a security lock.

[Supplementary Note 35]

The portable terminal device according to any one of supplementary notes 29 to 34, wherein a plurality of telephone dictionary data templates each corresponding to the ring type information are registered in the telephone dictionary, the telephone dictionary registering means selects a telephone dictionary data template corresponding to the ring type information included in the incoming call signal from the plurality of the telephone dictionary data templates, and registers the caller number, the caller text information, and the caller information image in the selected telephone dictionary data template.

[Supplementary Note 36]

The portable terminal device according to any one of supplementary notes 29 to 35, wherein the incoming telephone call is an incoming call from a nurse call extension unit in a nurse call system, and the caller information includes at least one of a name of a caller, information indicating a location where the nurse call extension unit is placed, and information indicating a medical specialty of the caller.

[Supplementary Note 37]

An incoming call history display method comprising:
receiving an incoming call signal including a caller number, caller information, and ring type information when an incoming telephone call is received,
generating caller text information based on at least one of the caller information and the ring type information,
registering the caller number and the caller text information in a telephone dictionary managed in the portable terminal device,
acquiring, from the telephone dictionary, the registered caller text information corresponding to the caller number, and displaying an incoming call screen including the caller text information,
associating the caller number which is a source of a call with the caller text information and storing the caller number and the caller text information in incoming call history information, and
deleting, after the incoming telephone call ends, the registered caller number from the telephone dictionary, and
acquiring, when an incoming call history including a number of a source of the incoming telephone call and a name of the source of the incoming is displayed, the caller text information from the incoming call history information and displaying the acquired caller text information as a name of the source of a call.

[Supplementary Note 38]

A program causing a processor to execute:
receiving an incoming call signal including a caller number, caller information, and ring type information when an incoming telephone call is received,
generating caller text information based on at least one of the caller information and the ring type information,
registering the caller number and the caller text information in a telephone dictionary managed in the portable terminal device,
acquiring, from the telephone dictionary, the registered caller text information corresponding to the caller number, and displaying an incoming call screen including the caller text information,
associating the caller number which is a source of a call with the caller text information and storing the caller number and the caller text information in incoming call history information, and
deleting, after the incoming telephone call ends, the registered caller number from the telephone dictionary, and
acquiring, when an incoming call history including a number of a source of the incoming telephone call and a name of the source of the incoming is displayed, the caller text information from the incoming call history information and displaying the acquired caller text information as a name of the source of a call.

REFERENCE SIGNS LIST

10: PORTABLE TERMINAL DEVICE
11: INCOMING CALL SIGNAL RECEPTION MEANS
12: IMAGE GENERATION MEANS
13: TELEPHONE DICTIONARY REGISTERING MEANS
14: TELEPHONE DICTIONARY
15: INCOMING CALL SCREEN DISPLAY MEANS
20: PORTABLE TERMINAL DEVICE
21: INCOMING CALL SIGNAL RECEPTION MEANS
22: TELEPHONE DICTIONARY REGISTERING MEANS
23: TELEPHONE DICTIONARY
24: INCOMING CALL SCREEN DISPLAY MEANS
25: INCOMING CALL HISTORY RECORDING MEANS
26: INCOMING CALL HISTORY DISPLAY MEANS
100: NURSE CALL SYSTEM
101: NC EXTENSION UNIT
102: NC BASE UNIT
103: NC CONTROLLER
104: PRIVATE BRANCH EXCHANGE
105: ACCESS POINT
150: PORTABLE TERMINAL DEVICE
151: OS
152: DEDICATED APPLICATION
153: CallKit
154: TELEPHONE DICTIONARY
155: NURSE CALL INCOMING CALL PROCESSING UNIT
156: INCOMING CALL SIGNAL RECEPTION UNIT
157: REGISTRATION DATA GENERATION UNIT
158: TELEPHONE DICTIONARY OPERATING UNIT
159: CallKit OPERATION UNIT
160: INCOMING CALL HISTORY RECODING UNIT

161: INCOMING CALL HISTORY INFORMATION
162: INCOMING CALL HISTORY DISPLAY UNIT
170: NETWORK INTERFACE
171: EXTERNAL INTERFACE

The invention claimed is:

1. A portable terminal device comprising:
a memory; and
a processor configured to:
   receive an incoming call signal including a caller number, caller information, and ring type information when an incoming telephone call is received from a nurse call extension unit in a nurse call system;
   generate caller text information based on at least one of the caller information and the ring type information included in the incoming call signal; and
   display an incoming call screen including the caller text information with a background color in accordance with the ring type information.

2. The portable terminal device according to claim 1, wherein
the processor is further configured to
   display the incoming call screen with the red background color when the ring type information indicates that the urgency is high.

3. The portable terminal device according to claim 1, wherein
the processor is further configured to
   display the incoming call screen with the black background color when the ring type information indicates that the urgency is low.

4. The portable terminal device according to claim 1, wherein
the caller information includes at least one of a name of a caller, information indicating a location where the nurse call extension unit is placed, and information indicating a medical specialty of the caller.

5. An incoming call screen display method, comprising:
receiving an incoming call signal including a caller number, caller information, and ring type information when an incoming telephone call is received from a nurse call extension unit in a nurse call system;
generating caller text information based on at least one of the caller information and the ring type information included in the incoming call signal; and
displaying an incoming call screen including the caller text information with a background color in accordance with the ring type information.

6. An incoming call screen display method according to claim 5, wherein
   displaying the incoming call screen with the red background color when the ring type information indicates that the urgency is high.

7. An incoming call screen display method according to claim 5, wherein
   displaying the incoming call screen with the black background color when the ring type information indicates that the urgency is low.

8. An incoming call screen display method according to claim 5,
wherein
   the caller information includes at least one of a name of a caller, information indicating a location where the nurse call extension unit is placed, and information indicating a medical specialty of the caller.

9. A non-transitory computer readable medium storing a program causing a processor to execute:
receiving an incoming call signal including a caller number, caller information, and ring type information when an incoming telephone call is received from a nurse call extension unit in a nurse call system;
generating caller text information based on at least one of the caller information and the ring type information included in the incoming call signal; and
causing a frame work, to display an incoming call screen, which is configured to display the incoming call screen including the caller text information with a background color in accordance with the ring type information.

10. The non-transitory computer readable medium according to claim 9, wherein
   displaying the incoming call screen with the red background color when the ring type information indicates that the urgency is high.

11. The non-transitory computer readable medium according to claim 9, wherein
   displaying the incoming call screen with the black background color when the ring type information indicates that the urgency is low.

12. The non-transitory computer readable medium according to claim 9, wherein
   the caller information includes at least one of a name of a caller, information indicating a location where the nurse call extension unit is placed, and information indicating a medical specialty of the caller.

* * * * *